US012622988B2

(12) United States Patent
Pattai et al.

(10) Patent No.: US 12,622,988 B2
(45) Date of Patent: May 12, 2026

(54) APPARATUS FOR PLASMA STERILIZATION OF MEDICAL DEVICES

(71) Applicant: Loewenstein Medical Technology S.A., Luxembourg (LU)

(72) Inventors: Steffen Pattai, Koblenz (DE); Torsten Kurz, Kadenbach (DE); Lukas Wellmann, Bad Ems (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 784 days.

(21) Appl. No.: 17/823,282

(22) Filed: Aug. 30, 2022

(65) Prior Publication Data

US 2023/0061721 A1     Mar. 2, 2023

(30) Foreign Application Priority Data

Sep. 1, 2021     (DE) ......................... 102021004434.7
Sep. 14, 2021   (DE) ......................... 102021004655.2

(51) Int. Cl.
| *A61L 2/14* | (2006.01) |
| *A61L 2/20* | (2006.01) |
| *A61L 2/26* | (2006.01) |
| *A61L 103/15* | (2026.01) |
| *A61M 16/01* | (2006.01) |

(52) U.S. Cl.
CPC .................................... *A61L 2/14* (2013.01); *A61L 2/20* (2013.01); *A61L 2/26* (2013.01); *A61L 2103/15* (2026.01); *A61L 2202/11* (2013.01); *A61L 2202/13* (2013.01); *A61M 16/01* (2013.01)

(58) Field of Classification Search
CPC ................. A61L 2/14; A61L 2/20; A61L 2/26
See application file for complete search history.

(56) References Cited

U.S. PATENT DOCUMENTS

| 6,969,487 | B1 | 11/2005 | Sias et al. |
| 2011/0027125 | A1 | 2/2011 | Golkowski |
| 2021/0060193 | A1* | 3/2021 | Hancock ................... B08B 9/02 |

* cited by examiner

*Primary Examiner* — Sean E Conley
(74) *Attorney, Agent, or Firm* — Abel Schillinger, LLP

(57)     ABSTRACT

A system for sterilization of a medical device comprising at least one medical device and at least one sterilization device. The sterilization device comprises at least one plasma generator and at least one water source and/or water vapor source for providing water and/or water vapor. The sterilization device is configured to generate plasma-activated water vapor and the system is configured to at least partially conduct the plasma-activated water vapor through the medical device.

20 Claims, 6 Drawing Sheets

1

APPARATUS FOR PLASMA STERILIZATION OF MEDICAL DEVICES

CROSS-REFERENCE TO RELATED APPLICATIONS

The present application claims priority under 35 U.S.C. § 119 of German Patent Application Nos. 102021004434.7, filed Sep. 1, 2021, and 102021004655.2, filed Sep. 14, 2021, the entire disclosures of which are expressly incorporated by reference herein.

BACKGROUND OF THE INVENTION

1. Field of the Invention

The invention relates to an apparatus and method for sterilizing medical devices.

2. Discussion of Background Information

Besides the therapy of sleeping conditions, ventilators are commonly also used in the clinical setting, especially for respiratory diseases. It is unavoidable that parts of the gas-conducting components, for example the patient gas lines, become contaminated. Even if there is no contamination by pathogens, hygiene treatment of the ventilators is necessary after use.

Known methods for hygiene treatment are frequently complex and time-intensive and often also require at least partial dismantling of the devices. Moreover, the cleaning methods are frequently complicated and require aggressive chemicals for sufficient treatment to be achieved. Accordingly, the devices are not available for a relatively long time after use.

In view of the foregoing, it would be advantageous to have available a ventilation device that can be treated in a cost-effective manner and with little effort.

SUMMARY OF THE INVENTION

The invention provides a system for sterilization of a medical device, comprising at least one medical device and at least one sterilization device, wherein the sterilization device comprises at least one plasma generator and at least one water source and/or water vapor source for provision of water and/or water vapor. The sterilization device is designed to generate plasma-activated water vapor and the system is configured to at least partially conduct the plasma-activated water vapor through the medical device.

In some embodiments, the system is characterized in that the medical device is a ventilator, wherein the ventilator comprises at least one patient gas pass and the system is configured to at least partially conduct the plasma-activated water vapor through the patient gas pass.

In some embodiments, the system is characterized in that the system comprises a waste gas treatment which is configured and designed to treat the plasma-activated water vapor.

In some embodiments, the system is characterized in that the waste gas treatment comprises at least one filter and/or one plasma generator.

In some embodiments, the system is characterized in that the waste gas treatment is configured and designed to filter out active species from the plasma-activated water vapor.

In some embodiments, the system is characterized in that the waste gas treatment is configured and designed to convert long-lived active species into short-lived species.

In some embodiments, the system is characterized in that the sterilization device is integrated into the ventilator.

In some embodiments, the system is characterized in that the ventilator comprises a respiratory gas source, wherein the respiratory gas source is connected to the sterilization device and is configured to supply the sterilization device with working gas.

In some embodiments, the system is characterized in that the sterilization device is connectable to an expiration port and/or an inspiration port of the patient gas pass for sterilization and the system is configured and designed in such a way that, during the sterilization, plasma-activated water vapor is conducted from the sterilization device into the patient gas pass through the expiration port and/or the inspiration port.

In some embodiments, the system is characterized in that the sterilization device is connected to the patient gas pass during the sterilization in such a way that the plasma-activated water vapor is conducted into the patient gas pass through the expiration port and is conducted out of the patient gas pass through the inspiration port, wherein patient gas pass is designed and configured in such a way that the plasma-activated water vapor flows through the entire patient gas pass during the flow from expiration port to inspiration port.

In some embodiments, the system is characterized in that the ventilator comprises a suction unit which is configured and designed to suck the plasma-activated water vapor through the patient gas pass.

In some embodiments, the system is characterized in that there is integrated into the ventilator a waste gas treatment which is configured and designed to treat the plasma-activated water vapor which is conducted out of the patient gas pass through the inspiration port and/or the expiration port.

In some embodiments, the system is characterized in that the sterilization device and the waste gas treatment are connected to the patient gas pass within the ventilator in such a way that plasma-activated water vapor flows through the entire patient gas pass during the sterilization.

In some embodiments, the system is characterized in that the sterilization device is de signed to convey the plasma-activated water vapor through the patient gas pass.

In some embodiments, the system is characterized in that a user interface is arranged in the system and a duration and/or a mode of sterilization is settable via the user interface.

In some embodiments, the system is characterized in that the user interface is integrated into the ventilator.

In some embodiments, the system is characterized in that the system is configured and designed to automatically carry out the sterilization after starting via the user interface.

In some embodiments, the system is characterized in that the ventilator is configured to check the requirements at the start of sterilization and to enable the sterilization only when all the requirements have been met.

In some embodiments, the system is characterized in that the user interface is configured to display a status of the sterilization.

In some embodiments, the system is characterized in that the sterilization device is configured to provide a permanent stream of plasma-activated water vapor and/or to convey it through the patient gas pass in a first sterilization mode.

In some embodiments, the system is characterized in that the sterilization device is configured to provide a pulsed stream of plasma-activated water vapor and/or to convey it through the patient gas pass in a second sterilization mode.

In some embodiments, the system is characterized in that the first and/or second sterilization mode is selectable via the user interface.

In some embodiments, the system is characterized in that the medical device is an incubator, wherein the incubator comprises at least one incubation space and the incubation space has at least one supply line and one discharge line and plasma-activated water vapor is conducted into the incubation space via the supply line and is discharged via the discharge line.

In some embodiments, the system is characterized in that there is arranged in the incubator at least one circulation unit which is designed to circulate the plasma-activated water vapor in the incubation space.

The invention also provides a method for sterilizing a medical device. The method is characterized in that a plasma-activated water vapor is generated via a sterilization device and the plasma-activated water vapor is at least partially conducted through the medical device.

In some embodiments, the method is characterized in that the medical device is a ventilator and the plasma-activated water vapor is at least partially conducted through a patient gas pass of the ventilator.

In some embodiments, the method is characterized in that the plasma-activated water vapor is conducted through the entire patient gas pass, wherein the plasma-activated water vapor is conducted through a waste gas treatment after flow through the patient gas pass.

It should be noted that the features listed individually in the claims can be combined with one another in any technically expedient fashion and indicate further configurations of the invention. The description provides additional characterization and specification of the invention, particularly in conjunction with the figures.

It should further be noted that an "and/or" conjunction which is used herein and which is found between two features and links them together should always be interpreted as meaning that only the first feature may be present in a first configuration of the subject matter of the invention, only the second feature may be present in a second configuration, and both the first and the second feature may be present in a third configuration.

A medical device can be considered to be any device for a medical application. In particular, ventilators and incubators are meant by the inventors.

The incubators can include not only incubators, but also warmers for newborns.

A ventilator is to be understood to mean any device which assists a user or patient with natural respiration, undertakes the ventilation of the user or living being (e.g., patient and/or newborn and/or premature baby) and/or is used for respiratory therapy and/or influences the respiration of the user or patient in another way. By way of example, but without being an exhaustive list, these include CPAP and BiLevel machines, anesthetic machines, respiratory therapy devices, (clinical, outpatient or emergency) ventilators, high-flow therapy devices and cough machines.

Ventilators can also be understood to mean diagnostic devices for ventilation. Said diagnostic devices can generally be used to measure medical and/or respiration-based parameters of a living being. These also include devices which can measure and optionally process medical parameters of patients in combination with respiration or only in relation to respiration.

Unless expressly described otherwise, a patient interface can be understood to mean any peripheral device which is designed for interaction of the measurement device with a living being, in particular for therapeutic or diagnostic purposes. In particular, a patient interface can be understood to mean a mask of a ventilator or a mask connected to the ventilator. Said mask can be a full-face mask, i.e. a mask surrounding the nose and mouth, or a nasal mask, i.e. a mask only surrounding the nose. Tracheal tubes or cannulas and so-called nasal cannulas can be used as a mask or patient interface, too. In some cases, the patient interface can also be a simple mouthpiece, for example a tube, through which the living being at least exhales and/or inhales.

According to the invention, respiratory gas can be any kind of gas and/or gas mixture which can be inhaled by a patient without harming said patient. For example, the respiratory gas used can be ambient air. Synthetic air and/or air from a compressed gas line or gas cylinder can be considered to be respiratory gas, too. Mixtures of nitrogen and oxygen and optionally further gases are usable as respiratory gas, too. In some embodiments, one or more anesthetic gases can also be added to the respiratory gas.

According to the invention, respiratory gas source refers quite generally to a gas source via which respiratory gas is conveyed. For example, a respiratory gas source can also comprise a gas mixer for adding, for example, oxygen and/or anesthetic gas to a respiratory gas. The respiratory gas can, for example, be conveyed to a patient by a conveyance unit. In some embodiments, the conveyance unit can be equated with the respiratory gas source, for example as a fan which conveys ambient air into the ventilator. Respiratory gas source and conveyance unit can definitely also be separate, for example in the case of ventilators having a (partially) closed gas loop. In this case, the conveyance unit is designed in such a way that the patient gas is conveyed within the loop. Said patient gas is to be understood to mean the gas or gas mixture which is conveyed within the loop. According to the inventors, the gas or gas mixture which is supplied to the gas loop in order, for example, to replace consumed oxygen and/or other gases is referred to as fresh gas.

The inventive system is designed for effective and cost- and time-efficient hygiene treatment of a ventilator present in the system. To this end, the sterilization device is, by way of example, configured to generate a plasma-activated water vapor. To this end, a small amount of water and/or water vapor is injected into a plasma stream. Compared to a pure plasma, the plasma-activated water vapor also contains long-lived active species which, for example, allow a longer action time in the ventilator. Long-lived active species are, for example, ozone and/or hydroxyl. On average, long-lived species do not decompose in under 60 seconds. According to the invention, it is contemplated that at least the patient gas pass, especially the part which comes into contact with the exhaled air of the patient unfiltered, is subjected to hygiene treatment by the plasma-activated water vapor.

In some embodiments, entry of the active species into the ambient air is avoided by conducting the plasma-activated water vapor, after it has flowed through the patient gas pass, through a waste gas treatment, for instance a filter and/or a second plasma generator which converts the long-lived species into short-lived species. On average, short-lived species decompose within <60 seconds. If there is provided in the ventilator a waste air, though which the exhaled air of the patient is conducted out of the ventilator during ventilation, the waste gas treatment can be integrated upstream of and/or in the waste air path.

To convey the plasma-activated water vapor through the patient gas line, use can be made of, for example, a suction unit, which can be integrated into the ventilator. By means of said suction unit, it is also possible after the sterilization for gas to be further sucked through the patient gas pass and/or a negative pressure to be generated in order to get the patient gas pass as free of plasma-activated water vapor as possible. Moreover, it is contemplated that, for this purpose, use can also be made of after-flushing with respiratory gas, fresh gas or working gas through the patient gas pass.

In order not to damage components sensitive to plasma and/or plasma-activated water vapor, they are decoupled from the patient gas pass, for example via valves, during the sterilization.

The working gas for the generation of plasma is, for example, provided via an external gas source, but can alternatively or additionally also be provided by the respiratory gas source of the ventilator.

In some embodiments of the system, the ventilator is in the form of an anesthetic machine and comprises not only the patient gas pass for machine ventilation, but also a patient gas pass for manual ventilation (e.g., via a bag valve mask) that is optionally connected to the machine patient gas pass. During machine ventilation, conveyance of patient gas is generally only possible through one of the two patient gas passes, while whichever is the other patient gas pass is closed, for example by valves. For the sterilization, the valves can be opened in such a way that simultaneous flow through the two patient gas passes (for the machine ventilation and for the manual ventilation) is possible. Alternatively or additionally, a sterilization mode can also be provided, in which plasma-activated water vapor flows through the patient gas passes one after the other or alternatingly.

The ventilator can definitely also be a very rudimentary device which essentially comprises a patient gas pass and a respiratory gas source. If the system comprises such a ventilator design, it is possible for the sterilization device to operate completely independently of the ventilator, i.e., to have its own power supply and gas supply and to also be controlled independently of the ventilator. For example, the ventilator is then connected to the sterilization device in such a way that the plasma-activated water vapor is guided through the patient gas pass of the ventilator by means of the sterilization device.

The sterilization is, for example, controlled via the control unit of the ventilator. If the sterilization device is not integrated into the ventilator, a connection via interfaces between the ventilator and the sterilization device is additionally provided. Inputs relating to the sterilization, for example concerning the duration and/or a mode, are possible via the user interface. In some embodiments, the flow and/or an average residence time of the plasma-activated water vapor in the patient gas pass can also be settable. The amount of water or water vapor injected into the plasma stream can be settable, too. Further possible sterilization settings can, for example, also concern after-flushing of the patient gas pass with working gas and/or fresh gas and/or respiratory gas.

By way of example, the valves of the ventilator are switched via the control unit in such a way that the plasma-activated water vapor is conveyed solely through the patient gas pass. In addition, the supply of working gas to the sterilization device is controlled via the control unit. In some embodiments, the sensor unit and/or the detection unit are designed and configured in such a way that the sterilization is monitored. For example, in the event of a detected leakage, through which plasma-activated water vapor can escape from the system and/or the ventilator, the sterilization can be interrupted, and an alarm can optionally be generated.

Beside control via the ventilator, the sterilization device can also have its own control units, which, for example, at least partially control the generation of the plasma-activated water vapor and/or the conveyance/conduction thereof through the patient gas pass. In addition, a user interface can be arranged on the sterilization device. Via said user interface, inputs for controlling the sterilization device can be made, for example. The sterilization device can at least be switched on and off via this optional user interface.

If no suction unit is integrated in the ventilator, the plasma-activated water vapor is conveyed through the patient gas pass by the pressure of the working gas of the sterilization device. Alternatively or additionally, it is contemplated that the conveyance of the plasma-activated water vapor is at least supported by the conveyance unit and/or an additional conveyance unit just for the sterilization, for instance a fan.

The invention further also relates to a method for hygiene treatment of a ventilator.

In this case, the method comprises at least the steps of generating a plasma-activated water vapor and conveying the plasma-activated water vapor through at least parts of the patient gas pass of the ventilator.

The generation of the plasma-activated water vapor can be divided into a first step, in which a cold plasma stream is generated from a working gas in a plasma generator, and into a second step, in which small amounts of water are injected into the plasma stream, thereby giving rise to the plasma-activated water vapor.

To convey the plasma-activated water vapor through the patient gas pass, the plasma-activated water vapor is conducted into the patient gas pass. In some embodiments, the patient gas pass is designed and configured in such a way that the plasma-activated water vapor is conducted in via one port and is conducted out of the patient gas pass via another port, with the plasma-activated water vapor flowing through the complete patient gas pass.

In an optional further method step, the plasma-activated water vapor, after it has flowed through the patient gas pass, is treated via a waste gas treatment. Said treatment can comprise filtering out long-lived active species and/or plasma treatment to convert the long-lived active species into short-lived species.

Optionally, the sterilization can be followed by flushing of the patient gas pass with working gas, fresh gas and/or respiratory gas.

In some embodiments, the ventilator checks whether all the requirements for starting a sterilization have been met. Requirements which must be met include, for example, executed connection of the sterilization device to the patient gas pass, supply of the sterilization device with working gas and water, connection of the patient gas pass to the suction unit and/or the waste gas treatment, no connection between patient gas pass and a patient, and supply of power to ventilator and sterilization device. The system or the respiratory gas pass can be tested for leaks, too.

BRIEF DESCRIPTION OF THE DRAWINGS

Further advantages and features of the present invention will become clear from the description of the illustrative embodiments, which are explained below with reference to the accompanying drawings. In the drawings.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
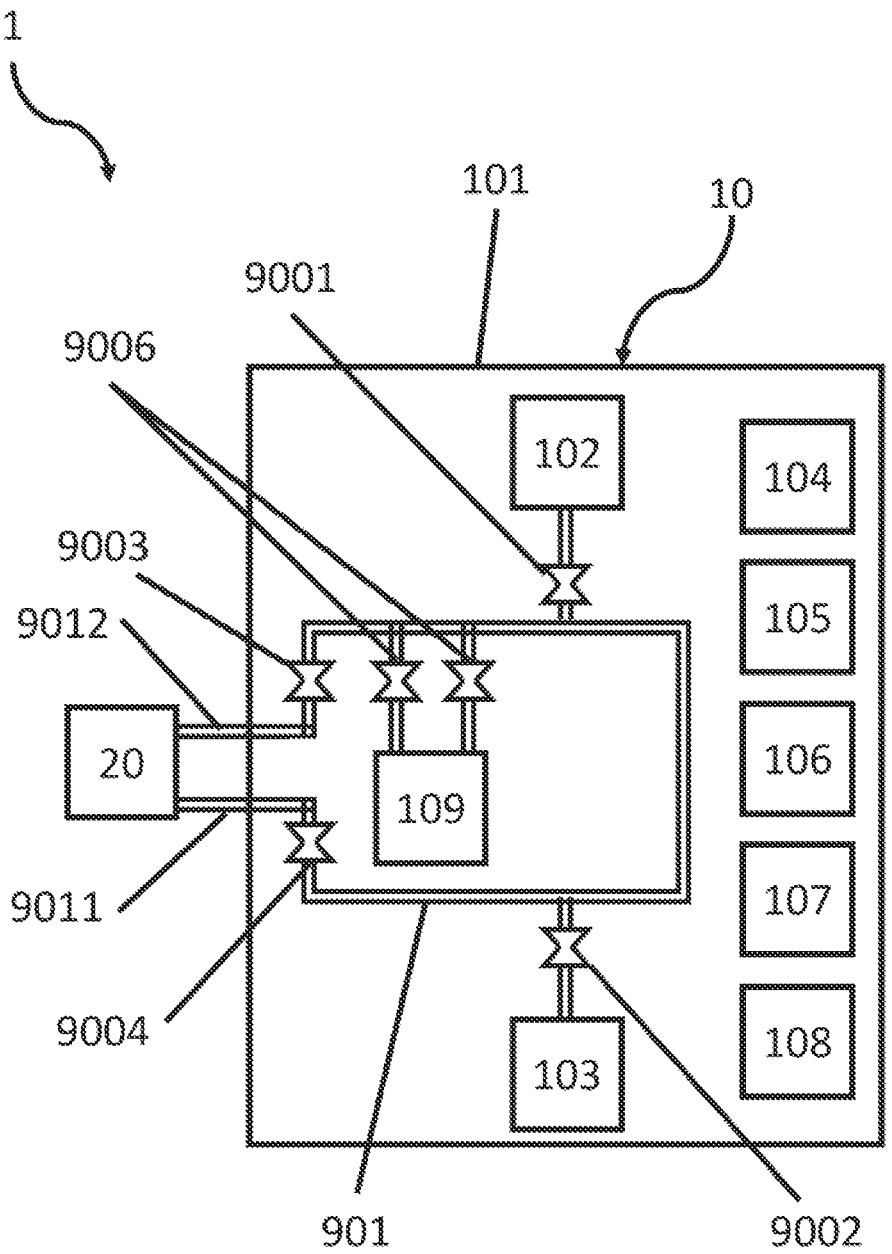
FIG. 1 shows schematically a first exemplary embodiment of the system of the invention.

FIG. 1 shows an exemplary embodiment of the system, wherein the ventilator 10 is in the form of an anesthetic machine and has an at least partially closed patient gas loop. The ventilator 10 has, by way of example, at least one housing 101, in which a respiratory gas source 102, a conveyance unit 103, a control unit 104, a sensor unit 105, an evaluation unit 106, a user interface 107, a detection unit 108 and a $CO_2$ absorber 109 are arranged. Arranged in the housing 101 of the ventilator 10 is a patient gas pass 901 through which the patient gas is conducted. Via an inspiration port 9011, the patient gas can be conducted to the patient via a patient interface, for example a ventilation mask. Via the expiration port 9012, coming from the patient, the gas exhaled by the patient is reconducted into the patient gas pass 901 in the ventilator 10. Connected to the patient gas pass 901 are the respiratory gas source 102, the conveyance unit 103 and the CO2 absorber 109, with, by way of example, the valves 9001, 9002 and 9006 being arranged between the patient gas pass 901 and the connected components. As needed, the valves 9001, 9002 and 9006 can be opened, closed or partially opened/closed.

Besides the components listed, it is self-evident that further components can also be present in the ventilator 10, for example a gas flow compensation (for instance, a bag valve mask) or ports and/or patient gas paths for manual ventilation.

The respiratory gas source 102 is, by way of example, configured in such a way that, if needed, it can feed fresh gas or respiratory gas into the patient gas loop or the patient gas pass 901. To this end, the respiratory gas source 102 is, by way of example, connected to a compressed air source, for example a compressed air cylinder and/or a house connection (hospital). Moreover, there is provided an oxygen source, likewise via a gas cylinder or a house connection, and optionally also at least one source of an anesthetic gas.

The supply of fresh gas into the patient gas pass is, for example, controlled via the valve 9001 and via the respiratory gas source 102.

The conveyance unit 103 is configured to convey a respiratory gas stream or patient gas stream through the patient gas pass 901. For example, the conveyance unit 103 is in the form of a bellows which, as a result of contraction, for example driven by a drive gas, conveys the patient gas to the patient through the patient gas pass 901. As a result of expiration by the patient, the bellows is re-expanded and the respiratory cycle can start again. In some embodiments, the conveyance unit 103 is additionally or alternatively in the form of a fan.

The control unit 104 is configured to control at least the respiratory gas source 102, the conveyance unit 103 and the valves 9001, 9002, 9003, 9004, 9006. To this end, the control unit 104 can, for example, be divided into multiple control units, each of which is configured to control one component of the ventilator 10 and/or the system 1. In some embodiments, the control unit 104 is also configured to control the sterilization device 20. The control unit 104 is, by way of example, also configured to process values, data and information from the sensor unit 105, the evaluation unit 106, the user interface 107 and/or the detection unit 108 and/or to use them as a basis for controlling the components of the ventilator 10 and/or the system 1.

The sensor unit 105 is, for example, configured to acquire measurement values and measurement data via sensors connected thereto, which, for example, are arranged in the ventilator 10 or, generally, in the system 1. Said measurement values and measurement data can, for example, encompass the ventilation of the patient, such as, for example, flow, pressure, gas composition, temperature, blood oxygen concentration, heartbeat and/or humidity. Further data and values optionally also associated with the ventilation indirectly can, by way of example, be acquired, too, via the sensor unit 105.

The evaluation unit 106 is, by way of example, designed to process, further process, analyze and/or assess, inter alia, the measurement values and/or measurement data from the sensor unit 105 and/or other data sources, such as, for example, data and information input via a user interface 107.

In the system 1 or, by way of example, in the ventilator 10, there is arranged a user interface 107 which comprises at least an input device and/or display device. Via the input device, for example a keyboard and/or (rotary) knobs and/or a touch-sensitive surface (touchscreen), it is possible to input data, information and values, and also parameters for controlling the ventilator 10 and/or the system 1. A display device can, for example, be a display or else an analog display or simple illuminated symbols. The display device is, for example, configured to display data and/or values and/or information which concern, inter alia, the status of the system 1 and/or the ventilation of a patient. In some embodiments, inputs for controlling the sterilization device 20 are moreover possible via the user interface 107.

The detection unit 108 is, by way of example, configured to detect technical problems of the ventilator 10. By way of example, technical problems may include a low battery level, faults in the electronics, a defective rechargeable battery, a defective component, a power outage, an accessory that does not work correctly, an implausible measurement value or a departure from the allowed temperature range. Should a technical problem be detected, the detection unit 108 can display and/or convey an alarm on the ventilator 10 and/or via an interface (not depicted). In some embodiments, the detection unit 107 is also configured to detect technical problems throughout the system 1, for example technical problems of a sterilization device 20 arranged externally to the ventilator 10 and, for example, connected to the ventilator 10.

The $CO_2$ absorber 109 of the ventilator 10 is configured to at least partially filter out $CO_2$ from the patient gas. For example, the $CO_2$ absorber 109 is filled with a material which can absorb $CO_2$. To this end, the patient gas is, for example, conducted in such a way that it flows around and/or flows through the material in the $CO_2$ absorber 109.

In the case of the partially closed patient gas loop, the patient gas is conveyed to the patient through the patient gas pass 901 via the inspiration port 9011 by means of the conveyance unit 103. Through the expiration port 9012, the patient gas exhaled by the patient is reconducted into the patient gas pass 901 of the ventilator 10. The flow direction of the patient gas within the patient gas pass 901 is, for example, controlled via the valves 9003 and 9004, and so, for example, the valve 9003 is closed during inspiration so that the patient gas can only be conveyed to the patient via the inspiration port 9011. By contrast, the valve 9004 is closed during expiration by the patient so that the exhaled air is conducted into the patient gas pass 901 through the expiration port 9012. In some embodiments, the valves 9003 and 9004 are, in particular, in the form of check valves. By way of example, the valves 9001, 9002 and 9006 are arranged between the patient gas pass 901 and the respiratory gas source 102, the conveyance unit 103 and the $CO_2$ absorber 109. The patient gas exhaled by the patient is, by way of example, conducted through a $CO_2$ absorber 109 in order to remove the exhaled $CO_2$ from the patient gas. For example, in order to resupply the consumed oxygen and/or also consumed anesthetic gas, fresh gas or a relevant gas mixture can be introduced into the gas loop via the respiratory gas source 102.

In the embodiment of the system 1 that is depicted in FIG. 1 by way of example, a sterilization device 20 is connected to the ventilator 10. By way of example, the sterilization device 20 is connected to the patient gas pass 901 of the ventilator 10 via the inspiration port 9011 and the expiration port 9012.

A sterilization device 20 is arranged in the system 1 for sterilization or hygiene treatment of the ventilator 10. In the exemplary embodiment depicted, the sterilization device 20 is arranged outside the housing 101 of the ventilator 10 and gaseously connected to the patient gas pass 901 via the inspiration port 9011 and the expiration port 9012.

The sterilization device 20 comprises at least one plasma generator. A cold plasma is generated from a working gas via the plasma generator. For example, use is made here of a standard method for generation of a cold plasma. Said plasma generator is designed in such a way that arc discharge is prevented. For example, the plasma generator is configured to generate a cold plasma via a dielectric barrier discharge (DBD). To this end, a high voltage, for example a sinusoidal alternating voltage or a pulsed direct voltage, is applied at two electrodes. A gas space is present between the electrodes, with one of the electrodes being separated from the gas space by a dielectric layer. The applied high voltage causes ionization of at least some of the gas in the gas space between the electrodes and, subsequently, so-called gas discharge and formation of the plasma.

What can be used as the working gas of the sterilization device 20 is, for example, ambient air, which is provided at a pressure within a range between 2 bar and 10 bar, especially between 4 bar and 6 bar. In some embodiments, synthetic air and/or compressed air and/or other gas mixtures can also be used as the working gas. The working gas is, for example, provided by a gas supply, for instance gas cylinders and/or a compressor and/or a house gas line, that is additionally connected to the sterilization device 20. In some embodiments of the system 1, the working gas is supplied by the ventilator 10, for example at least in part from the respiratory gas source 102, which is connected to the sterilization device 20 via an additional line. In this case, the gas mixture can, for example, be adapted; especially if the respiratory gas source 102 is used for supply of working gas, the gas mixture can be adjusted in such a way that no anesthetic gases are added to the working gas.

In the exemplary embodiment, a small amount of water, for example <5 ml per minute, is injected into the plasma stream which is formed, in order to generate a plasma-activated water vapor. To this end, the sterilization device 20 comprises at least one water source. The water source can, for example, be fed by a water connection or an integrated water tank. In some embodiments, the water is injected into the plasma in a fine jet. Dropwise injection or atomization of water is conceivable, too. In some embodiments, the water is injected into the plasma stream as water vapor. To this end, the sterilization device 20 optionally comprises a vaporizer. The use of water vapor at least as part of the working gas is, in principle, conceivable, too. To this end, the working gas which is conducted into the plasma generator already has water vapor added thereto or it consists solely of water vapor.

For example, the plasma-activated water vapor is conducted into the patient gas pass 901 via the expiration port 9012. The conveyance of the plasma-activated water vapor is, for example, primarily effected by the applied pressure of the working gas. In the embodiment in FIG. 1 that is depicted by way of example, the plasma-activated water vapor is conducted out of the patient gas pass 901 through the inspiration port 9011. During the sterilization, the valves 9001, 9002 and 9006 are closed, so that the plasma-activated water vapor does not come into contact with components of the ventilator 10 that, for example, do not have sufficient corrosion resistance or can be damaged by the plasma-activated water vapor in another way. In some embodiments, at least the conveyance unit 103 and/or the CO2 absorber 109 are configured and designed in such a way that they can be separated from the ventilator 10 and exchanged. In some embodiments, the conveyance unit 103 and/or the CO2 absorber are configured and designed in such a way that they, too, can be subjected to hygiene treatment with the plasma-activated water vapor.

Because the plasma-activated water vapor is conducted in through the expiration port 9012 and is conducted out through the inspiration port 9011, this ensures that the entire loop, especially the patient gas pass 901, can be subjected to hygiene treatment with the plasma-activated water vapor. Here, the direction of flow is, by way of example, configured and designed in the same manner as the direction of flow of the patient gas during ventilation, which patient gas is conducted by the patient into the patient gas pass 901 through the expiration port 9012 and is conducted in the patient gas pass 901 to the inspiration port 9011. In some embodiments, the plasma-activated water vapor is oppositely conducted, i.e., from the inspiration port 9011 through the patient gas pass 901 to the expiration port 9012.

The valves 9003 and 9004 are, by way of example, open during the sterilization, so that the plasma-activated water vapor can flow freely through the patient gas pass 901. By way of example, the plasma-activated water vapor is conducted into the patient gas pass 901 via the expiration port

9012 and conducted out of the patient gas pass 901 via the inspiration port 9011. In some embodiments, it is also possible for the opposite direction of flow to be chosen or for the direction of flow to be changed after some time in a recurrent manner.

If the pressure of the working gas is used as the main driving force for conducting/conveying the plasma-activated water vapor into and/or through the patient gas pass, it is, for example, possible for the plasma and/or the plasma-activated water vapor to be generated first while the valve 9003 downstream of the expiration port 9012 remains closed. If the valve 9003 is then opened, the plasma-activated water vapor can, for example, flow into the patient gas pass 901 through a pressure gradient between sterilization device 20 and patient gas pass 901. Alternatively or additionally, it is also possible for the pressure of the working gas to be permanently maintained and for the plasma-activated water vapor to continuously flow through the patient gas pass 901 owing to the pressure.

Since the plasma-activated water vapor may comprise some long-lived species such as ozone and hydroxyl, after-cleaning of the plasma-activated water vapor may be necessary after it has flowed through the patient gas pass 901. The goal here is that said long-lived species are not released into the ambient air and, for example, do not harm the staff involved in the cleaning. To this end, the plasma-activated water vapor is conducted out of the patient gas pass 901 through the inspiration port 9011 and, for example, back into the sterilization device 20. In some embodiments, a waste gas treatment is provided in the sterilization device 20. The waste gas treatment can, for example, comprise a filter, for instance loaded with activated carbon, which appropriately cleans the plasma-activated water vapor. To this end, in some embodiments, it is also possible to contemplate use of a catalyst which converts the long-lived, active species. Alternatively or additionally, it is also possible to provide a second plasma generator through which the plasma-activated water vapor is conducted, i.e., is used as working gas, in order to convert the long-lived species into short-lived species. In some embodiments, the second plasma generator generates a plasma stream, through which the plasma-activated water vapor escaping from the patient gas pass 901 as waste air is conducted. The short-lived species which are formed by the renewed plasma treatment decompose within a short time (for instance, under 60 seconds).

Alternatively or additionally, an arrangement of a suction device in the sterilization device 20 can also be realized in order to convey the plasma-activated water vapor through the patient gas pass 901. In this case, the sterilization device 20 is connected to the patient gas pass 901 in such a way that the suction can, by way of example, suck the plasma-activated water vapor through the patient gas pass 901 via the inspiration port 9011. In the case of an embodiment with a suction device, the waste gas treatment is, for example, arranged in such a way that the plasma-activated water vapor or the waste gas which is conducted out of the patient gas pass 901 via the inspiration port 9011 is drawn through the waste gas treatment comprising, for example, a filter device and/or a plasma treatment.

In some embodiments, the sterilization device 20 comprises its own conveyance unit which conveys the plasma-activated water vapor through the patient gas pass 901. In some embodiments, the conveyance unit 103 of the ventilator 10 is configured in such a way that it, too, can be treated with the plasma-activated water vapor without being damaged. In such a case, the conveyance of the plasma-activated water vapor through the patient gas pass 901 can also be performed by the conveyance unit 103.

Two sterilization modes can be contemplated in particular. In a first mode, plasma-activated water vapor is flushed pulse-wise through the patient gas pass 901. For example, the valves 9003 and 9004 are each briefly opened so that the plasma-activated water vapor can flow into the patient gas pass 901. For a certain time, which is optionally settable, the valves 9003 and 9004 are reclosed, so that the plasma-activated water vapor is in the patient gas pass 901 and can have some effect. Opening of the valves 9003 and 9004 allows an after-flow of fresh plasma-activated water vapor. This cycle can be repeated multiple times, for example over a period of 10 to 60 minutes or longer.

In another sterilization mode, plasma-activated water vapor is permanently flushed through the patient gas pass. To this end, the valves 9003 and 9004 are permanently open and the plasma-activated water vapor is continuously conveyed through the patient gas pass 901.

In some embodiments, at least the patient gas pass 901 can be flushed with gas after the completion of sterilization. For example, to this end, the working gas can be conveyed through the patient gas pass 901 by the sterilization device 20, during which the plasma generator is inactive and there is also no feeding of water and/or water vapor. In some embodiments, it is also contemplated that, alternatively or additionally, fresh gas is conducted through the patient gas pass 901 from the respiratory gas source 102.

The sterilization device 20 has, by way of example, its own power supply, gas sources and water sources. Moreover, the sterilization device 20 can have control units which are designed to control the generation and/or conveyance of the plasma-activated water vapor. Moreover, inputs for controlling the sterilization device 20 can be made via a user interface. The sterilization device 20 can at least be switched on and off, or activated and deactivated, via a user interface.

In some embodiments, the ventilator 10 and the sterilization device 20 are connected to one another via an interface. By way of example, it is thus possible to realize control of the sterilization device 20 via the ventilator 10. Alternatively or additionally, a connection between the ventilator 10 and the sterilization device 20 can also make it possible to achieve at least partial control of the valves of the ventilator 10 by the sterilization device 20.

In some embodiments, the sterilization device 20 also receives a supply of power and/or a supply of gas and/or a supply of water from the ventilator 10, in addition to a connection for control by the ventilator 10. In the ventilator 10, it is also possible to provide a suction unit 110 (not depicted in FIG. 1) which is used for conveyance of the plasma-activated water vapor through the patient gas pass 901. For example, the suction unit 110 is directly connected to the patient gas pass 901. The suction unit 110 can also comprise an additional port via which the inspiration port 9011 is connected to the suction unit 110 during the sterilization.

In some embodiments, the sterilization device 20 is part of the ventilator 10. For example, the sterilization device 20 is integrated into the housing 101 of the ventilator 10, and so both the components of the ventilator 10 and the sterilization device 20 are arranged in the housing 101. The sterilization device 20 is then, for example, arranged in such a way that the sterilization device 20 can be connected to the expiration port 9012 via at least one port and plasma-activated water vapor is thus conducted into the patient gas pass 901. If the sterilization device 20 is integrated into the ventilator 10, it is, for example, also possible to effect complete control of sterilization via the ventilator 10 or the user interface 107 of the ventilator 10.

Figure 2:
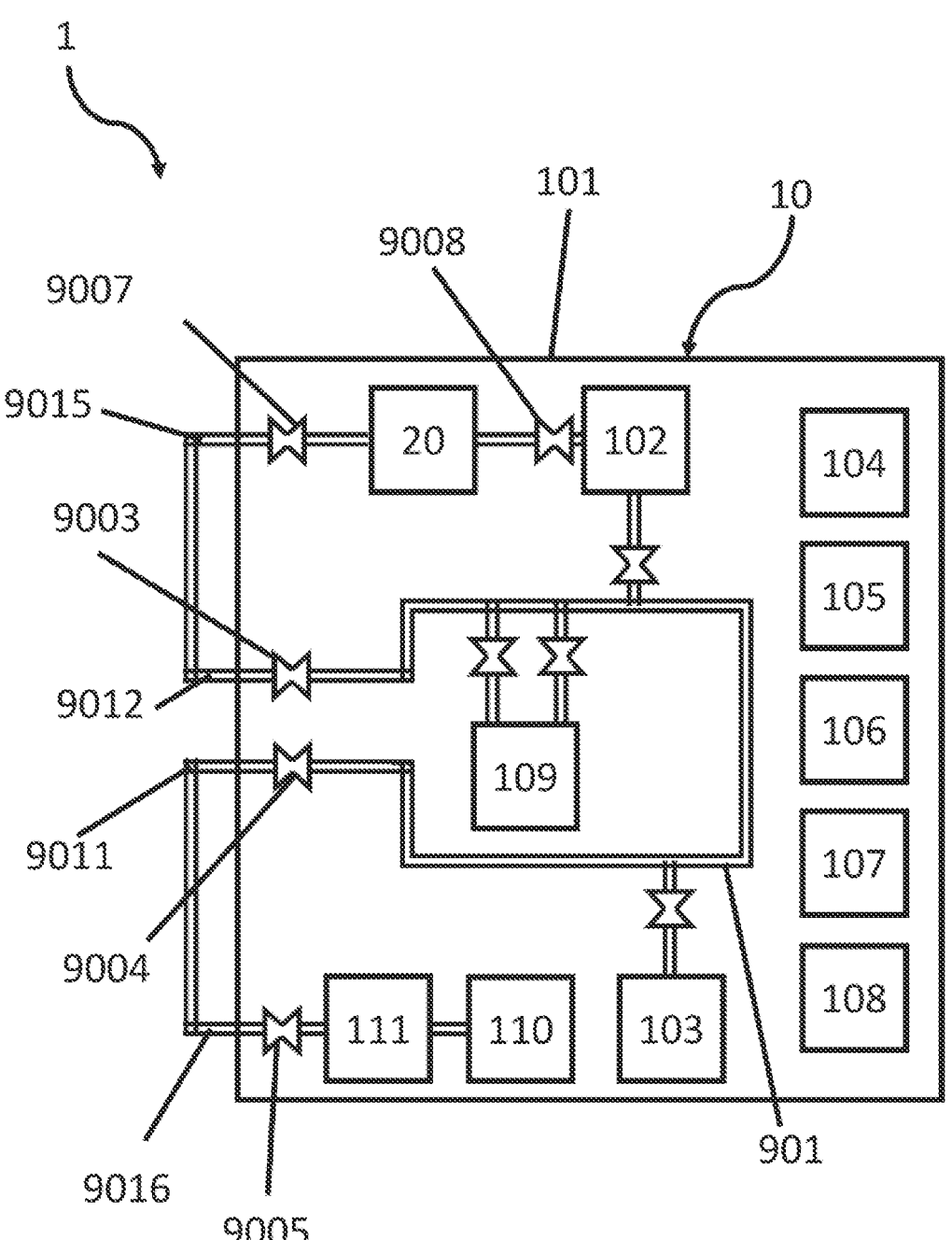
FIG. 2 shows schematically a second exemplary embodiment of the system of the invention.

FIG. 2 schematically depicts an exemplary embodiment of the system 1, wherein the ventilator 10 has an integrated suction unit 110 and the sterilization device 20 is integrated into the ventilator 10. Analogously to the embodiment depicted in FIG. 1, the ventilator 10 is in the form of an anesthetic machine and, unless explicitly described otherwise, has at least the same functionality. In general, an anesthetic machine according to the prior art is concerned, the differences according to the invention being described in what follows.

The sterilization device 20 is configured and designed to generate plasma-activated water vapor. The working gas for generation of the cold plasma in the sterilization device is, by way of example, supplied by the respiratory gas source 102. In some embodiments, the respiratory gas source 102 also comprises a source of anesthetic gas, there being no anesthetic gas conducted to the sterilization device 20 for the sterilization. The conveyance of gas from the respiratory gas source 102 to the sterilization device 20 can, for example, be controlled by the valve 9008; via the valve 9008, it is at least possible to control whether gas is conducted from the respiratory gas source 102 to the sterilization device 20. In some embodiments, the sterilization device 20 has a gas connection independent of the respiratory gas source 102. The supply of water to the sterilization device 20 is, for example, achieved via a water tank integrated into the ventilator 10 or into the sterilization device 20 and/or achieved by a connection to an external water supply.

For the sterilization, the sterilization port 9015 going out from the sterilization device 20 is connected to the expiration port 9012. As a result of this connection, the plasma-activated water vapor can be conducted into the patient gas pass 901 when valves 9007 and 9003 are open.

The suction unit 110 of the ventilator 10 is, inter alia, configured to be used for suction of secretion, for example from the respiratory tract of a patient. To this end, there is connected to the suction port 9016 an appropriate collection container into which the secretion is sucked. For example, there is arranged between suction port 9016 and suction unit 110 a valve 9005 via which the suction can be at least partially controlled. The suction unit 110 comprises, by way of example, a vacuum pump which can be used to generate a negative pressure which is used for suction.

During the sterilization, the suction unit 110 can be used to convey the plasma-activated water vapor through the patient gas pass 901. To this end, the suction port 9016 is connected to the inspiration port 9011. In the embodiment depicted in FIG. 2 by way of example, a waste gas treatment 111 is arranged between the suction port 9016 and the suction unit 110. After it has been conducted through the patient gas pass 901, the plasma-activated water vapor is conducted through the waste gas treatment 111. In the waste gas treatment 111, for example in the form of a filter and/or plasma generator, the plasma-activated water vapor is treated in that at least some of the long-lived active species are filtered out or converted into short-lived species which decompose, on average, within a time of <60 seconds. The filter material used can, for example, be activated carbon. The waste gas treatment 111 can, for example, also be used to treat the gas which is sucked in by the suction unit 110 with the suction of secretion, before said gas is released into the ambient air. In some embodiments, the waste gas treatment 111 has a bypass, so that gas or the plasma-activated water vapor is treated by the waste gas treatment 111 only during the sterilization.

The integration of the suction unit 110 into the ventilator 10 means that the suction unit optionally arranged in the sterilization device 20 in the embodiment depicted in FIG. 1 can be done away with.

The sterilization is, for example, controlled via the control unit 104. Inputs relating to the sterilization, for example concerning the duration and/or a mode, are possible via the user interface 107. In some embodiments, the flow and/or an average residence time of the plasma-activated water vapor in the patient gas pass 901 can also be settable. The amount of water or water vapor injected into the plasma stream can be settable, too. By way of example, the valves of the ventilator 10 are switched via the control unit 104 in such a way that the plasma-activated water vapor is conveyed solely through the patient gas pass 901. In addition, the supply of working gas to the sterilization device 20 is controlled via the control unit 104. In some embodiments, the sensor unit 105 and/or the detection unit 108 are designed and configured in such a way that the sterilization is monitored. For example, in the event of a detected leakage, through which plasma-activated water vapor can escape from the system 1 and/or the ventilator 10, the sterilization can be interrupted, and an alarm can optionally be generated.

Figure 3:
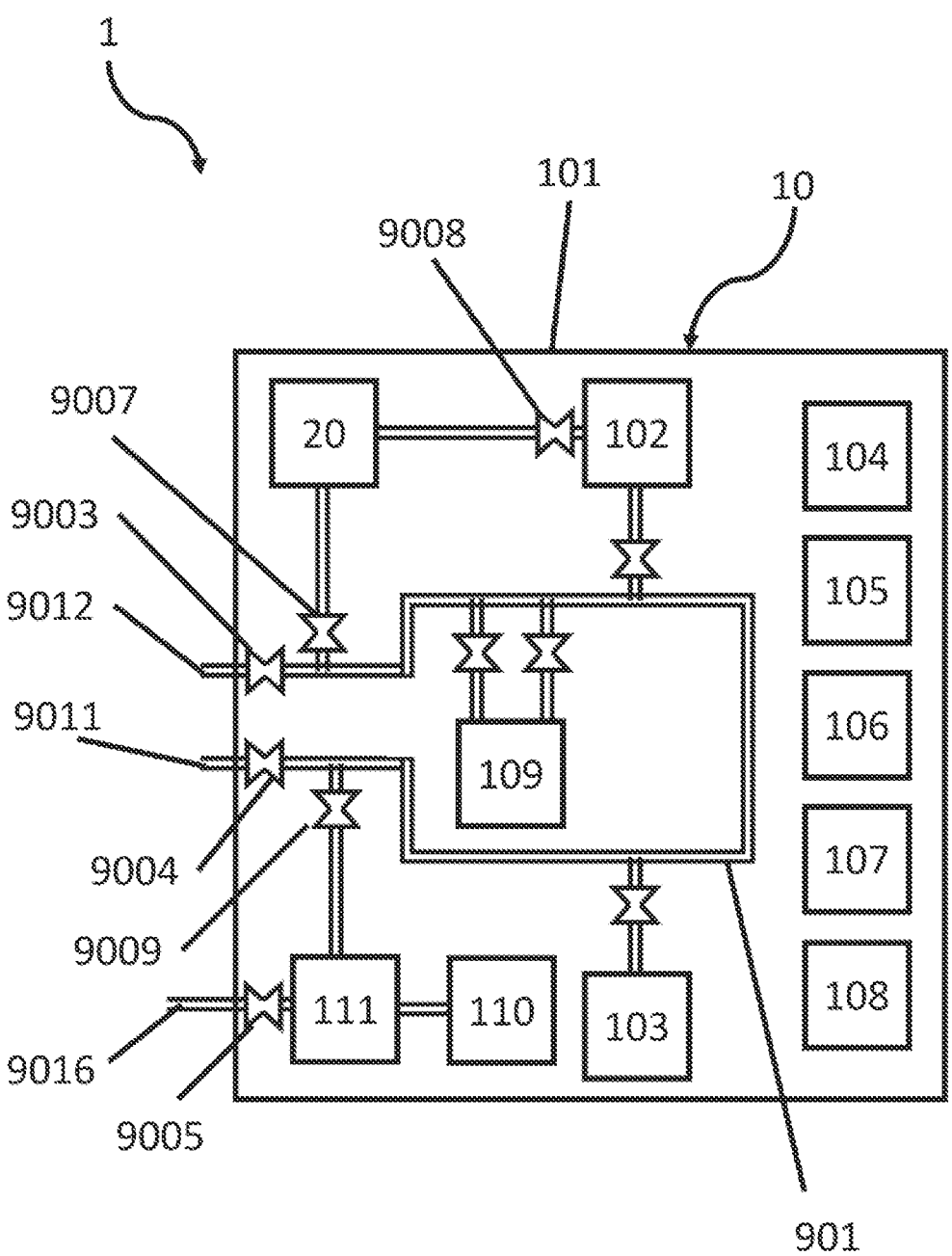
FIG. 3 shows schematically a third exemplary embodiment of the system of the invention.

FIG. 3 shows a schematic depiction of an exemplary embodiment of the system 1, in which the ventilator 10 is in the form of an anesthetic machine and the sterilization device 20 and a suction unit 110 are integrated into the ventilator 10. Here, the major functional features of the ventilator 10 correspond to an anesthetic machine according to the prior art or as described in relation to FIG. 1 and/or FIG. 2.

The sterilization device 20 integrated into the ventilator 10 is configured and designed to generate plasma-activated water vapor under generation of a cold plasma. For example, the working gas which is used by the plasma generator of the sterilization device 20 for generation of the cold plasma is provided by the respiratory gas source 102. Additionally or alternatively, the sterilization device 20 can be supplied with the working gas via an externally connected gas source, for example gas cylinders, directly and independently of the respiratory gas source 102. A water tank and/or port for an external water source, integrated into the ventilator 10 or the sterilization device 20, is provided for supply of the sterilization device 20 with water.

During the ventilation of a patient, the valve 9008 between respiratory gas source 102 and sterilization device 20 and the valve 9007 between sterilization device 20 and patient gas pass 901 are closed. For the sterilization, the two valves 9007, 9008 are opened, so that working gas can be conducted to the sterilization device 20 and, from there, plasma-activated water vapor can be conducted into the patient gas pass 901. In some embodiments, the valves between the respiratory gas source 102, the conveyance unit 103 and the CO2 absorber 109 and the patient gas pass 901 are closed during the sterilization. In some embodiments, at least one from respiratory gas source 102, conveyance unit 103 and/or CO2 absorber 109 is stable with respect to the plasma-activated water vapor and can be integrated into the sterilization run.

Unlike the embodiment depicted in FIG. 2, the sterilization device 20 within the ventilator 10 is directly connected to the patient gas pass 901 and is not connected to the expiration port 9012 via ports outside the housing 101. Accordingly, the valve 9003 is closed during the sterilization, so that unwanted escape of the plasma-activated water vapor from the expiration port 9012 into the ambient air cannot occur. In some embodiments, the expiration port 9012 can, for example, be closed by a blind plug.

A suction unit 110, for example a vacuum pump, is further arranged in the ventilator 10. The suction unit 110 is, inter alia, provided for conveyance or suction of plasma-activated water vapor through the patient gas pass 901. Between patient gas pass 901 and suction unit 110, there is arranged a waste gas treatment 111, for example a filter and/or a plasma generator, which, inter alia, is provided for treatment of the plasma-activated water vapor which has been conducted through the patient gas pass 901. In this connection, what is meant by treatment is that long-lived, active species are filtered out and/or converted into short-lived species which decompose, on average, within <60 seconds. The suction unit 110 is directly connected to the patient gas pass 901, and so a connection between the inspiration port 9011 and a suction port does not have to be additionally established. If the suction unit 110 is directly connected to the patient gas pass, the valve 9004 on the inspiration port 9011 is closed during the sterilization.

In the ventilator 10, there is additionally provided a suction port 9016 which leads to the suction unit 110. By way of example, the connection between suction port 9016 and suction unit 110 passes through the waste gas treatment 111. In some embodiments, it is, however, also possible for a bypass to be provided and/or for the waste gas treatment 111 to be arranged in such a way that the suction port 9016 is directly connected to the suction unit 110. The suction port 9016 is, for example, used for connection of a collection container when using the suction unit 110 for suction of secretion from the patient during ventilation. Moreover, it is also possible for the suction unit 110 not to be connected to the patient gas pass 901 within the ventilator 10. In such a case, the suction port 9016 is connected to the inspiration port 9011. During the sterilization, the plasma-activated water vapor is then sucked through the patient gas pass 901 via the inspiration port 9011 when valve 9004 is open.

The connection between the sterilization device 20 and the patient gas pass 901 and the connection between the suction unit 110 and the patient gas pass 901 are, by way of example, arranged in such a way that the plasma-activated water vapor passes through the entire patient gas pass 901. To this end, the sterilization device 20 is, by way of example, connected to the patient gas pass 901 in the immediate vicinity of the expiration port 9012 and the suction unit 110 is connected to the patient gas pass 901 in the immediate vicinity of the inspiration port 9011 or connected to the patient gas pass 901 via the inspiration port 9011.

The sterilization is, for example, controlled via the control unit 104. Inputs relating to the sterilization, for example concerning the duration and/or a mode, are possible via the user interface 107. In some embodiments, the flow and/or an average residence time of the plasma-activated water vapor in the patient gas pass 901 can also be settable. The amount of water or water vapor injected into the plasma stream can be settable, too. By way of example, the valves of the ventilator 10 are switched via the control unit 104 in such a way that the plasma-activated water vapor is conveyed solely through the patient gas pass 901. In addition, the supply of working gas to the sterilization device 20 is controlled via the control unit 104. In some embodiments, the sensor unit 105 and/or the detection unit 108 are designed and configured in such a way that the sterilization is monitored. For example, in the event of a detected leakage, through which plasma-activated water vapor can escape from the system 1 and/or the ventilator 10, the sterilization can be interrupted, and an alarm can optionally be generated.

In some embodiments, the ventilator 10 does not have a suction unit 110. In the case of such embodiments, it is contemplated that, for example, a waste gas treatment 111 is integrated into the ventilator 10 and/or is connectable to the patient gas pass 901 via the inspiration port 9011. In some embodiments, it is contemplated that a suction unit, external to the ventilator 10, is connected to the inspiration port 9011 in order to convey the plasma-activated water vapor through the patient gas pass 901 or to support it in being conveyed.

Especially if no suction unit 110 is integrated in the ventilator 10, the plasma-activated water vapor is conveyed through the patient gas pass 901 by the pressure of the working gas of the sterilization device 20. Alternatively or additionally, it is contemplated that the conveyance of the plasma-activated water vapor is at least supported by the conveyance unit 103 and/or an additional conveyance unit just for the sterilization, for instance a fan.

In some embodiments, after the sterilization has been completed, working gas and/or fresh gas (e.g., respiratory gas from the respiratory gas source 102) is conveyed through the patient gas pass 901 for some time in order to flush possible residues of the plasma-activated water vapor, for instance ozone, out of the patient gas pass 901.

In some embodiments, the internal connection of the sterilization device 20 to the patient gas pass 901 allows automatic sterilization of the patient gas pass 901. In particular, the step of connecting the sterilization device 20 to the patient gas pass 901 is dispensed with. In the case of automatic sterilization, the control unit 104 is configured to switch the valves of the ventilator 10 in such a way that the plasma-activated water vapor, generated by the sterilization device 20, can be conveyed through the patient gas pass 901. The conveyance and generation of the plasma-activated water vapor is controlled according to the sterilization settings specified via the user interface 107. If the user interface 107 or the system 1 has a display, it is possible to display a status of the sterilization, at least as to whether the sterilization is currently being carried out and/or whether the sterilization has been completed.

The automatic sterilization can, for example, take place in such a way that a check is first made after activation to determine whether the valves are switched to allow conduction of the plasma-activated water vapor solely through the patient gas pass 901 and/or the components provided for the sterilization. Thereafter, the sterilization device 20 is activated and the plasma-activated water vapor is generated. Depending on the setting, a permanent stream of plasma-activated water vapor or a pulsed stream of plasma-activated water vapor is, for example, conveyed through the patient gas pass 901. The duration of sterilization can, for example, be selected via the user interface 107. After completion of the sterilization in the sense of the generation and conveyance of the plasma-activated water vapor, fresh gas and/or working gas can be conveyed through the patient gas pass 901 for a definable period of time.

Figure 4:
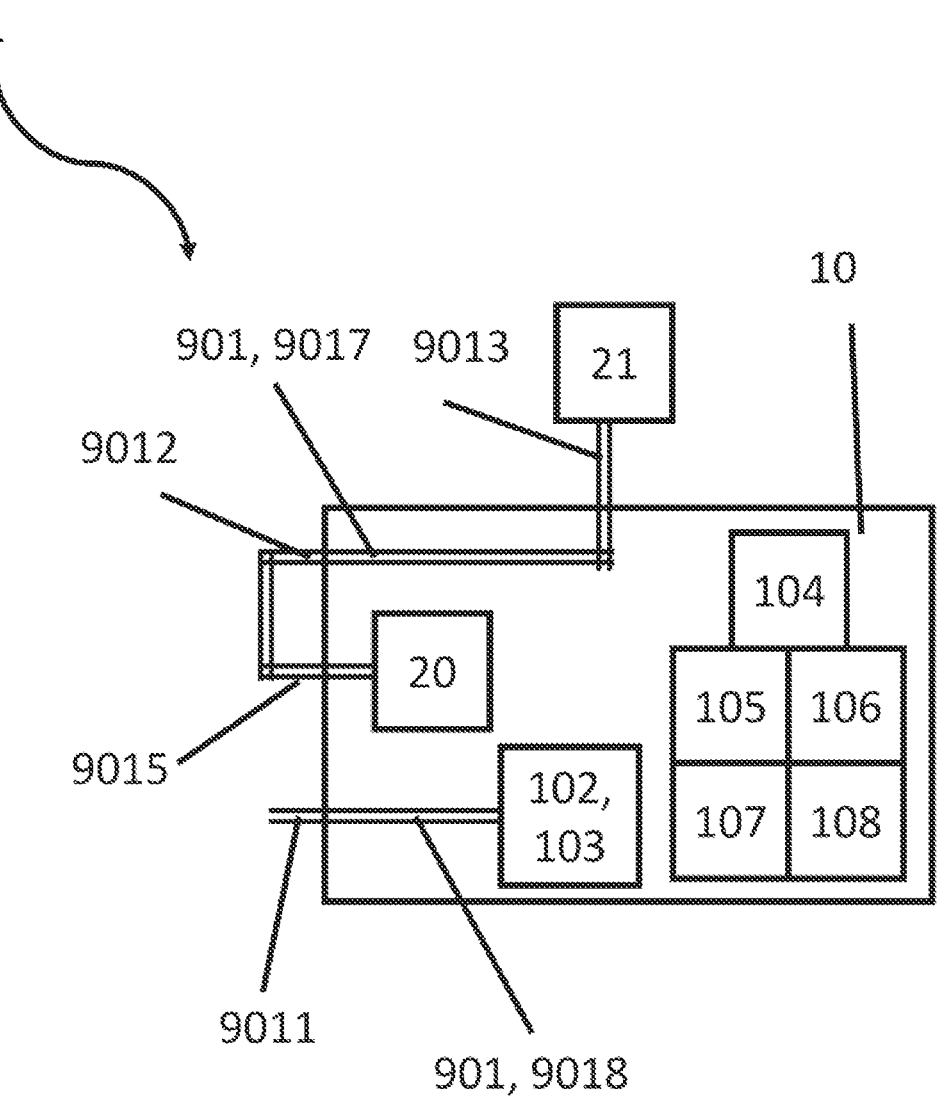
FIG. 4 shows schematically a fourth exemplary embodiment of the system of the invention.

FIG. 4 shows an exemplary embodiment of the system 1, in which the ventilator 10 is in the form of a home ventilator, for example for life-support ventilation and/or sleep therapy, or in the form of a ventilator for clinical ventilation. Here, the ventilator 10 substantially corresponds to a device according to the prior art and has at least a respiratory gas source 102, a conveyance unit 103, and a control unit 104, a sensor unit 105, an evaluation unit 106, a user interface 107 and a detection unit 108. The respiratory gas source 102 and the conveyance unit 103 can, for example, be in the form of one unit, for example in the form of a fan which sucks in ambient air and conveys it to the patient through the gas pass, for example the inspiration path 9018.

The control unit 104 is configured to control at least the respiratory gas source 102 and the conveyance unit 103. To this end, the control unit 104 can, for example, be divided into multiple control units, each of which is configured to control one component of the ventilator 10 and/or the system 1. In some embodiments, the control unit 104 is also configured to control the sterilization device 20. The control unit 104 is, by way of example, also configured to process values, data and information from the sensor unit 105, the evaluation unit 106, the user interface 107 and/or the detection unit 108 and/or to use them as a basis for controlling the components of the ventilator 10 and/or the system 1. If the sterilization device 20 is controlled via the ventilator 10, the ventilator 10 and the sterilization device 20 are, for example, connected to one another via an interface.

The sensor unit 105 is, for example, configured to acquire measurement values and measurement data via sensors connected thereto, which, for example, are arranged in the ventilator 10 or, generally, in the system 1. Said measurement values and measurement data can, for example, encompass the ventilation of the patient, such as, for example, flow, pressure, gas composition, temperature, blood oxygen concentration, heartbeat and/or humidity. Further data and values optionally also associated with the ventilation indirectly can, by way of example, be acquired, too, via the sensor unit 105.

The evaluation unit 106 is, by way of example, designed to process, further process, analyze and/or assess, inter alia, the measurement values and/or measurement data from the sensor unit 105 and/or other data sources, such as, for example, data and information input via a user interface 107.

In the system 1 or, by way of example, in the ventilator 10, there is arranged a user interface 107 which comprises at least an input device and/or display device. Via the input device, for example a keyboard and/or (rotary) knobs and/or a touch-sensitive surface (touchscreen), it is possible to input data, information and values, and also parameters for controlling the ventilator 10 and/or the system 1. A display device can, for example, be a display or else an analog display or simple illuminated symbols. The display device is, for example, configured to display data and/or values and/or information which concern, inter alia, the status of the system 1 and/or the ventilation of a patient. In some embodiments, inputs for controlling the sterilization device 20 are moreover possible via the user interface 107.

The detection unit 108 is, by way of example, configured to detect technical problems of the ventilator 10. By way of example, technical problems may include a low battery level, faults in the electronics, a defective rechargeable battery, a defective component, a power outage, an accessory that does not work correctly, an implausible measurement value or a departure from the allowed temperature range. Should a technical problem be detected, the detection unit 108 can display and/or convey an alarm on the ventilator 10 and/or via an interface (not depicted). In some embodiments, the detection unit 107 is also configured to detect technical problems throughout the system 1, for example technical problems of a sterilization device 20 arranged externally to the ventilator 10 and, for example, connected to the ventilator 10.

The ventilator 10 depicted in FIG. 4 by way of example has two essentially separate gas passes (expiration path 9017 and inspiration path 9018). Via the inspiration path 9018, respiratory gas is at least temporarily conveyed to the patient from the respiratory gas source 102 during ventilation. By way of example, the ventilator 10 is configured for ventilation via a two-hose system, wherein the air exhaled by the patient is conducted through one hose from the patient to the expiration port 9012 and through the expiration path 9017 in the ventilator 10 to the waste air 9013.

The ventilator 10 depicted by way of example additionally also comprises a sterilization device 20 for generation of plasma-activated water vapor for at least partial sterilization of the ventilator 10. In particular, the expiration path 9017 of the ventilator 10 can be subjected to hygiene treatment by the sterilization device 20. For the treatment, the sterilization port 9015 is also connected to the expiration port 9012. Via the sterilization device 20 for example, the plasma-activated water vapor is conveyed through the expiration path 9017 and provides hygiene treatment thereof. The plasma-activated water vapor can be conducted out of the expiration path 9017 via the waste air 9013. In some embodiments, it is necessary to treat the plasma-activated water vapor downstream of the waste air 9013. For example, a waste gas treatment 21 can be connected to the waste air 9013 to this end. The waste gas treatment 21 comprises, for example, a filter and/or a plasma generator in order to filter the long-lived active species, for instance ozone, out of the plasma-activated water vapor or to convert and/or neutralize said long-lived active species. In some embodiments, the waste gas treatment 21 can also be integrated into the ventilator 10.

The supply of working gas to the sterilization device 20 can, for example, be effected via additional gas sources, for instance gas cylinders, and/or via the respiratory gas source 102. For example, the sterilization device 20 can have a gas inlet which is connected to the inspiration port 9011.

It is also contemplated to include the inspiration path 9018 in the sterilization. For example, what is carried out to this end within the ventilator 10 is connection of the sterilization device 20 to the inspiration path 9018 and of the inspiration port 9011 to the expiration port 9012. Thus, the plasma-activated water vapor first flows through the inspiration path 9018, is then conducted through the inspiration port 9011 to the expiration port 9012, and lastly flows through the expiration path 9017 to the waste air 9013.

In some embodiments of the system 1, it is contemplated that a sterilization device 20 integrated into the ventilator 10 is also usable for sterilization of other devices, especially those through which a plasma-activated water vapor can flow.

Figure 5:
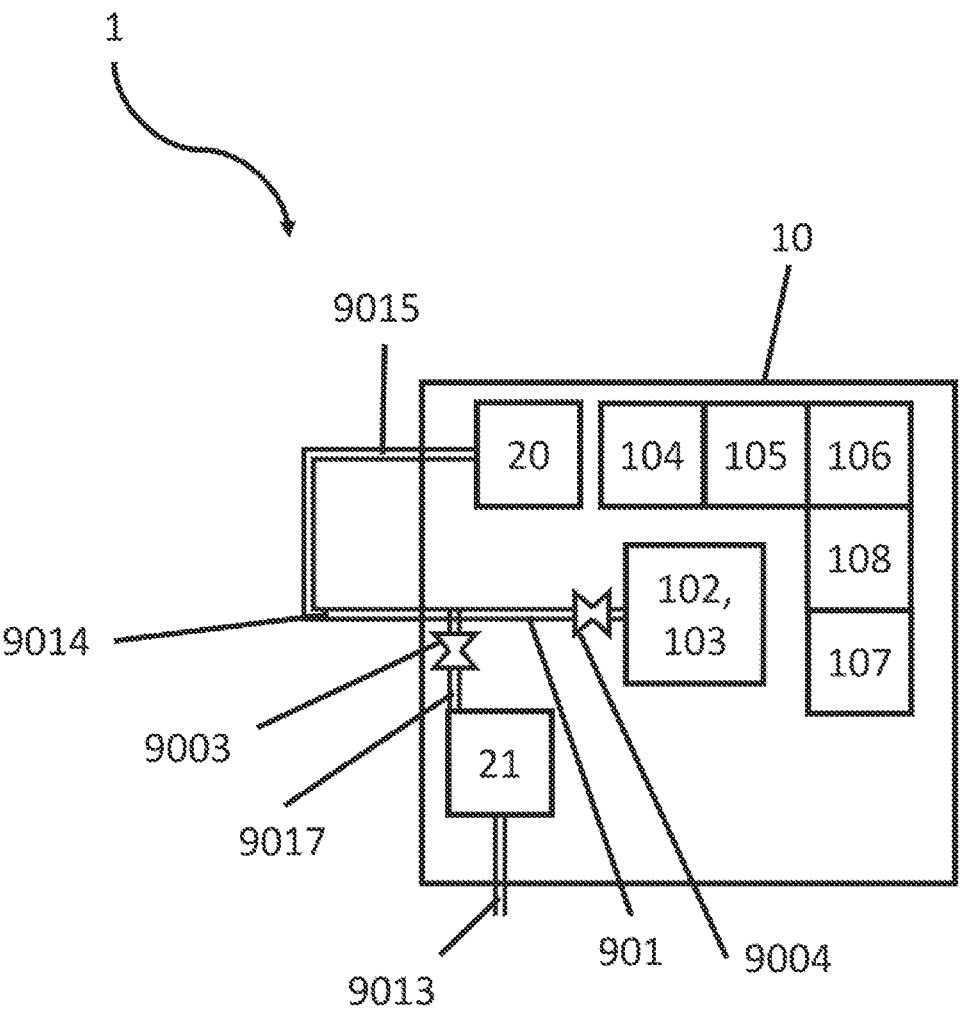
FIG. 5 shows schematically a fifth exemplary embodiment of the system of the invention.

A further exemplary embodiment of the system 1 is depicted in FIG. 5. Similar to the embodiment in FIG. 4, the ventilator 10 is in the form of a home ventilator or a ventilator for clinical ventilation. The ventilator 10 depicted is, by way of example, configured for operation in a one-hose system, for example with a leakage system or valve system. The patient interface is connected to the patient gas pass 901 of the ventilator 10 for ventilation via the patient port 9014. Here, the patient gas pass 901 splits into an inspiration path (not identified) and an expiration path 9017. Via the valves 9003, 9004, it is possible to control the respiratory gas flow for inspiration and expiration during ventilation. For example, during inspiration, the valve 9004 is opened and the valve 9003 is closed. As a result, respiratory gas is conveyed to the patient through the patient port 9014. During expiration by the patient, the valve 9004 is at least partially closed and the valve 9003 is opened, so that the respiratory gas flowing back can escape through the expiration path 9017.

A sterilization device 20 is integrated into the ventilator 10 for sterilization of the ventilator 10. The sterilization device 20 is designed and configured to generate plasma-activated water vapor and to at least partially convey said plasma-activated water vapor. Before the start of sterilization, the sterilization device 20 is at least connected to parts of the patient gas pass 901 by a connection between the sterilization port 9015 and the patient port 9014. Plasma-activated water vapor can flow through at least the expiration path 9017 of the patient gas pass 901. For example, the sterilization device 20 is configured to at least partially convey the plasma-activated water vapor through the patient gas pass 901. In order for the expiration path 9017 to be subjected to hygiene treatment or sterilization, the valve 9003 is opened for sterilization. This makes it possible for the plasma-activated water vapor to flow through the expiration path 9017.

In order to prevent the long-lived active species of the plasma-activated water vapor from being released into the ambient air, a waste gas treatment 21 is, by way of example, arranged downstream of the expiration path 9017. The waste gas treatment 21 comprises, for example, a filter which filters out the active species from the plasma-activated water vapor which was at least partially conducted through the patient gas pass 901. In some embodiments, the waste gas treatment 21 alternatively or additionally comprises a plasma generator which, through a plasma, converts the long-lived species of the plasma-activated water vapor into shorter-lived species which decompose, on average, within a time of <60 seconds. Via the waste air 9013, the plasma-activated water vapor or the waste air formed therefrom can then be conducted out of the ventilator 10 into the ambient air.

In some embodiments, the system 1, for example via the detection unit 108 and/or the sensor unit 105 together with the evaluation unit 106, is configured to test prior to the sterilization whether the sterilization device 20 is connected to the patient gas pass 901, for example via a short stream of working gas which is accordingly detected in the patient gas pass 901. If this test fails, an alarm or notice can be output and/or the sterilization device 20 can be blocked, for example. The block can then be removed by a successful test.

Figure 6:
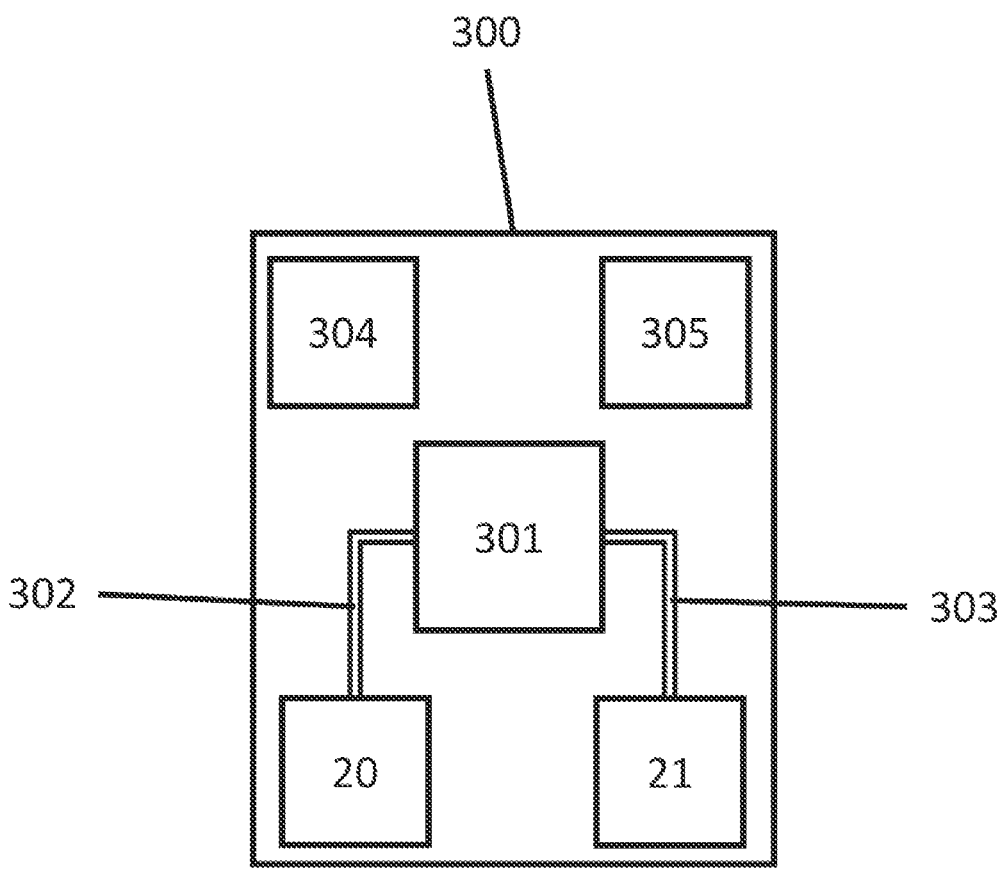
FIG. 6 shows schematically a sixth exemplary embodiment of the system of the invention.
Figure 6:

In FIG. 6, an exemplary embodiment of the system 1 can be seen, wherein the medical device is an incubator 300. The incubator can, for example, substantially correspond to an incubator known from the prior art. By way of example, the sterilization device 20 and a waste gas treatment 21 are provided within the incubator 300, but an external arrangement can also be possible. Moreover, the incubator 300 has an incubation space 301, for example for accommodation of a premature baby. The climate within the incubation space 301 is, for example, set via the climate unit 305. The climate unit 305 can, for example, be configured to set air humidity and/or temperature within the incubation space 301. Another possibility is that the climate unit 305 can set the gas composition within the incubation space 301, for example in the form of an increased oxygen concentration.

Via the supply line 302, plasma-activated water vapor can be conducted from the sterilization device 20 into the incubation space 301 to be sterilized. For example, via a circulation unit 304, it is ensured that the plasma-activated water vapor is distributed throughout the incubation space 301 and, in particular, reaches the surfaces.

Via a discharge line 303, the plasma-activated water vapor is discharged from the incubation space 301. For example, the waste gas treatment 21 can comprise a device for suction of the plasma-activated water vapor out of the incubation space 301. The waste gas treatment 21 additionally ensures that at least the long-lived species of the plasma-activated water vapor are neutralized and/or converted.

In some embodiments, the incubator 300 comprises safety measures, for instance motion sensors, which ensure that no living being, in particular no premature baby, is present in the incubation space 301 at the start of sterilization. Moreover, it can at least be determined that the incubation space 301 is closed, so that unwanted escape of plasma-activated water vapor is prevented. If it is determined that the incubation space 301 is not closed and/or if a living is detected, an alarm can be output and/or the start of sterilization can be prevented. A further possibility is that the incubator 300 has sensors which analyze the gas within the incubation space 301 and they can determine whether the incubation space 301 is free of residues harmful to health, in particular the plasma-activated water vapor. If residues harmful to health are determined, an alarm can be output and/or use of the incubator 300 can be blocked, for example, at least before start-up.

To sum up, the present invention provides:

1. A system for sterilization of a medical device, wherein the system comprises at least one medical device and at least one sterilization device, the at least one sterilization device comprising at least one plasma generator and at least one water source and/or water vapor source for providing water and/or water vapor and being configured to generate plasma-activated water vapor, and the system being configured to at least partially conduct the plasma-activated water vapor through the medical device.

2. The system of item 1, wherein the medical device is a ventilator which comprises at least one patient gas pass and the system is configured to at least partially conduct the plasma-activated water vapor through the patient gas pass.

3. The system of item 1 or item 2, wherein the system further comprises a waste gas treatment device which is configured and designed to treat the plasma-activated water vapor.

4. The system of item 3, wherein the waste gas treatment device comprises at least a filter and/or a plasma generator.

5. The system of item 3 or item 4, wherein the waste gas treatment device is configured and designed to filter out active species from the plasma-activated water vapor.

6. The system of at least one of items 3 to 5, wherein the waste gas treatment device is configured and designed to convert long-lived active species into short-lived species.

7. The system of at least one of items 2 to 6, wherein the at least one sterilization device is integrated into the ventilator.

8. The system of at least one of items 2 to 7, wherein the ventilator comprises a respiratory gas source which is connected to the sterilization device and is configured to supply the sterilization device with working gas.

9. The system of at least one of items 2 to 8, wherein the at least one sterilization device is connectable to an expiration port and/or an inspiration port of the patient gas pass for sterilization and the system is configured and designed in such a way that, during the sterilization, plasma-activated water vapor is conducted from the at least one sterilization device into the patient gas pass through the expiration port and/or the inspiration port.

10. The system of item 9, wherein the at least one sterilization device is connected to the patient gas pass during the sterilization in such a way that the plasma-activated water vapor is conducted into the patient gas pass through the expiration port and is conducted out of the patient gas pass through the inspiration port, the patient gas pass being designed and configured in such a way that the plasma-activated water vapor flows through the entire patient gas pass during a flow from expiration port to inspiration port.

11. The system of at least one of items 2 to 10, wherein the ventilator comprises a suction unit which is configured and designed to suck the plasma-activated water vapor through the patient gas pass.

12. The system of at least one of items 9 to 11, wherein there is integrated into the ventilator a waste gas treatment device which is configured and designed to treat the plasma-activated water vapor which is conducted out of the patient gas pass through the inspiration port and/or the expiration port.

13. The system of item 12, wherein the sterilization device and the waste gas treatment device are connected to the patient gas pass within the ventilator in such a way that during the sterilization plasma-activated water vapor flows through the entire patient gas pass.

14. The system of at least one of items 2 to 13, wherein the at least one sterilization device is configured to convey the plasma-activated water vapor through the patient gas pass.

15. The system of at least one of items 1 to 14, wherein a user interface is arranged in the system and a duration and/or a mode of sterilization is settable via the user interface.

16. The system of at least one of items 2 to 15, wherein the ventilator is configured to check the requirements at the start of the sterilization and to enable the sterilization only when all the requirements have been met.

17. The system of item 15, wherein the user interface is configured to display the status of the sterilization.

18. The system of at least one of claims 2 to 17, wherein the at least one sterilization device is configured to provide a permanent stream of plasma-activated water vapor and/or to convey it through the patient gas pass in a first sterilization mode.

19. The system of at least one of items 2 to 17, wherein the at least one sterilization device is configured to provide a pulsed stream of plasma-activated water vapor and/or to convey it through the patient gas pass in a second sterilization mode.

20. The system of item 18 or item 19, wherein the first and/or second sterilization mode is selectable via a user interface.

21. The system of at least one of items 1 and 3 to 6, wherein the at least one medical device is an incubator which comprises at least one incubation space comprising at least one supply line and one discharge line and plasma-activated water vapor is conducted into the incubation space via the supply line and is discharged via the discharge line.

22. The system of item 21, wherein there is arranged in the incubator at least one circulation unit which is configured to circulate the plasma-activated water vapor in the incubation space.

23. A method for sterilizing a medical device, wherein a plasma-activated water vapor is generated via a sterilization device and the plasma-activated water vapor is at least partially conducted through the medical device.

24. The method of item 23, wherein the medical device is a ventilator and the plasma-activated water vapor is at least partially conducted through a patient gas pass of the ventilator.

25. The method of item 24, wherein the plasma-activated water vapor is conducted through the entire patient gas pass, the plasma-activated water vapor being conducted through a waste gas treatment device after flow through the patient gas pass.

LIST OF REFERENCE SIGNS

1 System
10 Ventilator
20 Sterilization device
21 Waste gas treatment
101 Housing
102 Respiratory gas source
103 Conveyance unit
104 Control unit
105 Sensor unit
106 Evaluation unit
107 User interface
108 Detection unit
109 $CO_2$ absorber
110 Suction unit
111 Waste gas treatment
300 Incubator
301 Incubation space
302 Supply line
303 Discharge line
304 Circulation unit
305 Climate unit
901 Patient gas pass
9001 Valve
9002 Valve
9003 Valve
9004 Valve
9005 Valve
9006 Valve
9007 Valve
9008 Valve
9009 Valve
9011 Inspiration port
9012 Expiration port
9013 Waste gas
9014 Patient port
9015 Sterilization port
9016 Suction port
9017 Expiration path
9018 Inspiration path

What is claimed is:

1. A system for sterilization of a medical device, wherein the system comprises at least one medical device and at least one sterilization device, the at least one sterilization device comprising at least one plasma generator and at least one water source and/or water vapor source for providing water and/or water vapor and being configured to generate plasma-activated water vapor, and the system being configured to at least partially conduct the plasma-activated water vapor through the medical device, the medical device being a ventilator which comprises at least one patient gas pass and the system being configured to at least partially conduct the plasma-activated water vapor through the patient gas pass.

2. A system for sterilization of a medical device, wherein the system comprises at least one medical device and at least one sterilization device, the at least one sterilization device comprising at least one plasma generator and at least one water source and/or water vapor source for providing water and/or water vapor and being configured to generate plasma-activated water vapor, and the system being configured to at least partially conduct the plasma-activated water vapor through the medical device, the system further comprising a waste gas treatment device which is configured and designed to treat the plasma-activated water vapor.

3. The system of claim 2, wherein the waste gas treatment device comprises at least a filter and/or a plasma generator.

4. The system of claim 2, wherein the waste gas treatment device is configured and designed to filter out active species from the plasma-activated water vapor.

5. The system of claim 2, wherein the waste gas treatment device is configured and designed to convert long-lived active species into short-lived species.

6. The system of claim 1, wherein the at least one sterilization device is integrated into the ventilator.

7. The system of claim 1, wherein the ventilator comprises a respiratory gas source which is connected to the at least one sterilization device and is configured to supply the at least one sterilization device with working gas.

8. The system of claim 1, wherein the at least one sterilization device is connectable to an expiration port and/or an inspiration port of the patient gas pass for sterilization and the system is configured and designed in such a way that, during the sterilization, plasma-activated water vapor is conducted from the at least one sterilization device into the patient gas pass through the expiration port and/or the inspiration port.

9. The system of claim 8, wherein the at least one sterilization device is connected to the patient gas pass during the sterilization in such a way that the plasma-activated water vapor is conducted into the patient gas pass through the expiration port and is conducted out of the patient gas pass through the inspiration port, the patient gas pass being designed and configured in such a way that the plasma-activated water vapor flows through the entire patient gas pass during flow from expiration port to inspiration port.

10. The system of claim 1, wherein the ventilator comprises a suction unit which is configured and designed to suck the plasma-activated water vapor through the patient gas pass.

11. The system of claim 1, wherein there is integrated into the ventilator a waste gas treatment device which is configured and designed to treat the plasma- activated water vapor which is conducted out of the patient gas pass through an inspiration port and/or an expiration port.

12. The system of claim 11, wherein the sterilization device and the waste gas treatment device are connected to the patient gas pass within the ventilator in such a way that plasma-activated water vapor flows through the entire patient gas pass during the sterilization.

13. The system of claim 1, wherein the at least one sterilization device is configured to convey the plasma-activated water vapor through the patient gas pass.

14. The system of claim 1, wherein a user interface is arranged in the system and a duration and/or a mode of sterilization is settable via the user interface.

15. The system of claim 1, wherein the ventilator is configured to check the requirements at the start of sterilization and to enable the sterilization only when all the requirements have been met.

16. The system of claim 1, wherein the at least one sterilization device is configured to provide a permanent stream of plasma-activated water vapor and/or to convey it through a patient gas pass in a first sterilization mode or is configured to provide a pulsed stream of plasma-activated water vapor and/or to convey it through the patient gas pass in a second sterilization mode.

17. A system for sterilization of a medical device, wherein the system comprises at least one medical device and at least one sterilization device, the at least one sterilization device comprising at least one plasma generator and at least one water source and/or water vapor source for providing water and/or water vapor and being configured to generate plasma-activated water vapor, and the system being configured to at least partially conduct the plasma-activated water vapor through the medical device, the at least one medical device being an incubator which comprises at least one incubation space comprising at least one supply line and one discharge line and plasma-activated water vapor is being conducted into the incubation space via the supply line and being discharged via the discharge line.

18. The system of claim 17, wherein there is arranged in the incubator at least one circulation unit which is configured to circulate the plasma-activated water vapor in the incubation space.

19. A method for sterilizing a ventilator, wherein the ventilator is sterilized by operating the system of claim 1.

20. A method for sterilizing an incubator, wherein the incubator is sterilized by operating the system of claim 17.

\* \* \* \* \*